United States Patent
Ellis

(10) Patent No.: US 7,529,626 B1
(45) Date of Patent: *May 5, 2009

(54) METHOD OF INTEGRATION AND DISPLAYING OF INFORMATION DERIVED FROM A MUD GAS ISOTOPE LOGGING INTERPRETATIVE PROCESS IN ASSOCIATION WITH GEOPHYSICAL AND OTHER LOGS FROM OIL AND GAS DRILLING OPERATIONS

(76) Inventor: Leroy Ellis, 206 Hyde Park Dr., Richardson, TX (US) 75080

( * ) Notice: Subject to any disclaimer, the term of this patent is extended or adjusted under 35 U.S.C. 154(b) by 0 days.

This patent is subject to a terminal disclaimer.

(21) Appl. No.: 11/671,043

(22) Filed: Feb. 5, 2007

Related U.S. Application Data

(63) Continuation-in-part of application No. 10/952,136, filed on Sep. 28, 2004, now Pat. No. 7,174,254, which is a continuation-in-part of application No. 10/845,743, filed on May 14, 2004, now Pat. No. 7,124,030.

(51) Int. Cl.
*G01V 1/40* (2006.01)
(52) U.S. Cl. ............................................ 702/9
(58) Field of Classification Search ............... 702/6, 702/7, 8, 9, 11–15, 27, 30, 2; 166/262, 264, 166/402, 403; 73/1.85

See application file for complete search history.

(56) References Cited

U.S. PATENT DOCUMENTS 7,124,030 B2 * 10/2006 Ellis .............................. 702/9
7,174,254 B2 * 2/2007 Ellis .............................. 702/9

* cited by examiner

*Primary Examiner*—Edward Raymond
*Assistant Examiner*—Mohamed Charioui
(74) *Attorney, Agent, or Firm*—Michael Diaz

(57) ABSTRACT

A method of displaying well log isotopic information in a drilling operation of a target area. The method begins by profiling a plurality of mud gas samples through a well bore at a plurality of incremental depths of the well bore. The plurality of gas samples are analyzed to obtain a plurality of isotopic data points associated with hydrocarbon isotopic composition of the plurality of gas samples. The plurality of isotopic data points includes data associated with a composition of ethane and methane within each of the mud gas samples. The plurality of isotopic data points are plotted to determine geological information from the target area derived from the plotted plurality of isotopic data points. The plurality of isotopic data points is analyzed to geochemically interpret the geological information. The interpretation is then displayed with data from a mudlog and geophysical log.

8 Claims, 16 Drawing Sheets

| Depth (ft) | Total Gas (Rig. units) | Total HC (Lab. vol%) | Gas Composition Data | | | | | | | | Dryness %C1/Cn | Wetness %C2/Cn | Carbon Isotope Data | | |
|---|---|---|---|---|---|---|---|---|---|---|---|---|---|---|---|
| | | | %C1 | %C2 | %C3 | %iC4 | %NC4 | %iC5 | %NC5 | %C6+ | | | δ¹³C1 | δ¹³C2 | δ¹³C3 |
| 2150 | | 0.22 | 0.21 | | | | | | | | 97.54 | | -58.6 | | |
| 2300 | | 0.26 | 0.26 | | | | | | | | 100 | | -52.0 | | |
| 2450 | 19 | 0.99 | 0.97 | 0.014 | | | | | | | 98.26 | 1.42 | -45.1 | | |
| 2600 | | 1.10 | 1.08 | 0.012 | 0.001 | | 0.001 | 0.001 | 0.002 | | 98.19 | 1.09 | -44.1 | | |
| 2750 | 65 | 0.89 | 0.87 | 0.007 | | | | | | | 98.13 | 0.82 | -46.6 | | |
| 2900 | | 0.01 | 0.01 | | | | | | | | | | | | |
| 3050 | | 1.15 | 1.13 | 0.011 | 0.002 | 0.001 | 0.001 | 0.001 | 0.001 | | 98.42 | 0.96 | -48.4 | | |
| 3200 | 136 | 2.19 | 2.16 | 0.018 | 0.006 | 0.002 | 0.001 | 0.001 | 0.001 | | 98.79 | 0.82 | -49.2 | | |
| 3350 | | 0.79 | 0.79 | 0.003 | 0.004 | | | | | | 99.61 | 0.39 | -49.0 | | |
| 3500 | | 0.65 | 0.65 | 0.003 | 0.004 | 0.001 | | | | | 99.49 | 0.51 | -48.2 | | |
| 3650 | 54 | 0.83 | 0.82 | 0.008 | 0.002 | | | | | | 98.62 | 1.00 | -47.3 | | |
| 3800 | | 0.36 | 0.35 | 0.006 | 0.003 | 0.002 | 0.001 | 0.001 | 0.001 | | 96.77 | 1.58 | -46.6 | | |
| 3950 | | 0.82 | 0.78 | 0.024 | 0.013 | 0.003 | 0.002 | 0.002 | 0.002 | | 94.58 | 2.91 | -44.7 | | |
| 4100 | | 0.91 | 0.85 | 0.031 | 0.020 | 0.006 | 0.005 | 0.005 | 0.002 | | 93.51 | 3.41 | -44.4 | | |
| 4250 | | 0.97 | 0.87 | 0.051 | 0.025 | 0.006 | 0.005 | 0.005 | 0.005 | | 90.00 | 5.28 | -41.6 | | |
| 4293 | 550 | 7.73 | 6.71 | 0.470 | 0.280 | 0.071 | 0.061 | 0.061 | 0.074 | | 86.84 | 6.03 | -42.0 | -34.7 | -33.1 |
| 4311 | 760 | 9.81 | 8.59 | 0.600 | 0.340 | 0.081 | 0.063 | 0.063 | 0.070 | | 87.59 | 6.42 | -42.0 | | |
| 4326 | 120 | 1.30 | 1.16 | 0.071 | 0.038 | 0.010 | 0.008 | 0.008 | 0.010 | | 88.00 | 5.44 | -42.2 | | |
| 4360 | 200 | 2.44 | 2.14 | 0.140 | 0.081 | 0.019 | 0.018 | 0.018 | 0.021 | | 87.81 | 5.74 | -42.1 | | |
| 4423 | 125 | 1.42 | 1.24 | 0.086 | 0.047 | 0.011 | 0.010 | 0.010 | 0.012 | | 87.57 | 5.07 | -41.9 | | |
| 4514 | 700 | 13.41 | 12.6 | 0.430 | 0.220 | 0.037 | 0.025 | 0.025 | 0.030 | | 94.28 | 3.21 | -42.5 | -33.7 | -32.7 |
| 4565 | 390 | 4.57 | 3.97 | 0.280 | 0.100 | 0.037 | 0.029 | 0.029 | 0.034 | | 86.89 | 6.13 | -41.6 | | |
| 4576 | 850 | 11.16 | 9.91 | 0.610 | 0.400 | 0.077 | 0.053 | 0.053 | 0.059 | | 88.78 | 5.46 | -42.9 | -34.0 | -32.9 |
| 4600 | 220 | 2.38 | 2.11 | 0.140 | 0.080 | 0.015 | 0.011 | 0.011 | 0.014 | | 88.62 | 5.88 | -42.4 | | |
| 4650 | | 1.58 | 1.40 | 0.091 | 0.059 | 0.019 | 0.009 | 0.009 | 0.012 | | 88.43 | 5.75 | -42.6 | | |
| 4700 | | 2.61 | 2.33 | 0.140 | 0.078 | 0.015 | 0.014 | 0.014 | 0.018 | | 89.34 | 5.37 | -42.8 | | |
| 4714 | 1700 | 45.61 | 43.2 | 1.530 | 0.350 | 0.100 | 0.046 | 0.046 | 0.041 | | 94.71 | 3.35 | -43.9 | -33.5 | -32.5 |
| 4900 | 140 | 1.93 | 1.78 | 0.089 | 0.033 | 0.008 | 0.006 | 0.006 | 0.007 | | 92.32 | 4.62 | -43.8 | | |
| 5050 | | 0.30 | 0.27 | 0.014 | 0.005 | 0.002 | 0.003 | 0.003 | 0.004 | | 89.79 | 4.66 | -44.2 | | |

*FIG. 2A*

| | | | | | | | | | | | |
|---|---|---|---|---|---|---|---|---|---|---|---|
| 5350 | | 1.19 | 1.15 | 0.024 | 0.007 | | | | 96.73 | 2.02 | -46.9 |
| 5500 | 80 | 1.21 | 1.17 | 0.025 | 0.008 | 0.001 | 0.002 | 0.002 | 96.60 | 2.06 | -48.0 |
| 5650 | 80 | 1.38 | 1.33 | 0.033 | 0.012 | 0.002 | 0.002 | 0.003 | 96.73 | 2.40 | -48.1 |
| 5800 | 60 | 0.98 | 0.94 | 0.030 | 0.013 | | | | 95.54 | 3.05 | -48.4 |
| 5950 | | 0.95 | 0.89 | 0.037 | 0.017 | 0.001 | | | 94.06 | 3.91 | -48.5 |
| 6100 | 92 | 1.44 | 1.32 | 0.074 | 0.039 | 0.001 | 0.002 | 0.001 | 91.53 | 5.13 | -48.4 |
| 6250 | 42 | 0.80 | 0.73 | 0.039 | 0.023 | 0.004 | 0.002 | 0.001 | 91.11 | 4.87 | -47.6 |
| 6400 | | 1.10 | 0.96 | 0.074 | 0.048 | 0.003 | 0.005 | 0.002 | 87.02 | 6.71 | -48.8 |
| 6550 | | 0.72 | 0.62 | 0.047 | 0.033 | 0.007 | 0.004 | 0.005 | 86.65 | 6.57 | -48.4 |
| 6700 | | 1.16 | 1.02 | 0.078 | 0.047 | 0.004 | 0.004 | 0.004 | 87.83 | 6.72 | -48.9 |
| 6850 | | 0.83 | 0.72 | 0.060 | 0.037 | 0.006 | 0.004 | 0.003 | 86.67 | 7.22 | -48.7 |

*FIG. 2B*

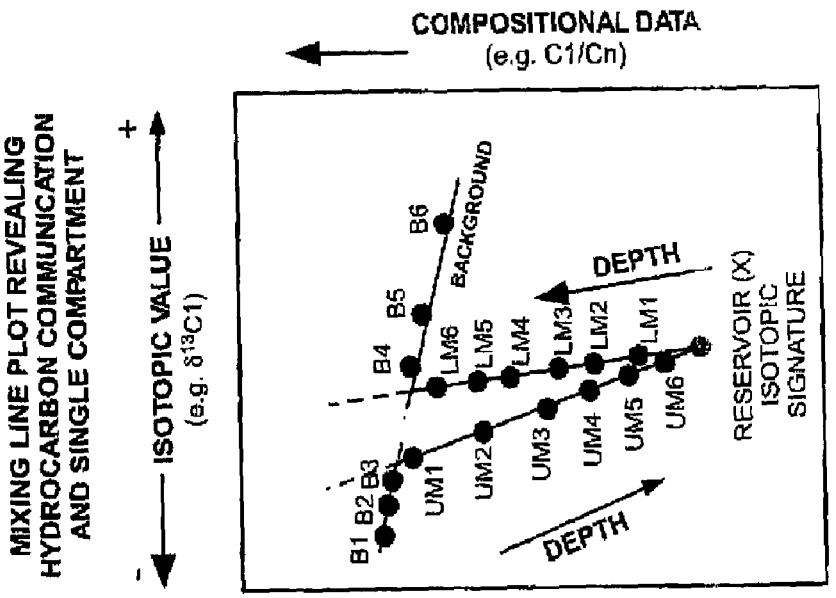
FIG. 5C
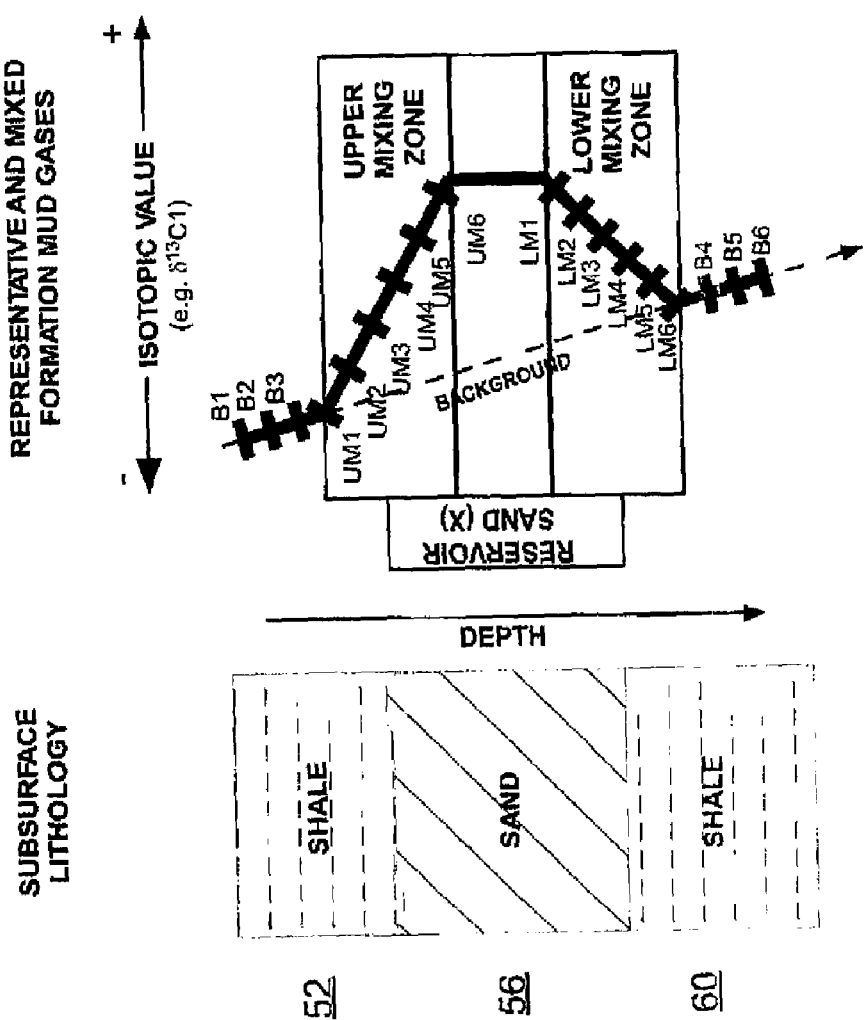
FIG. 5B
FIG. 5A

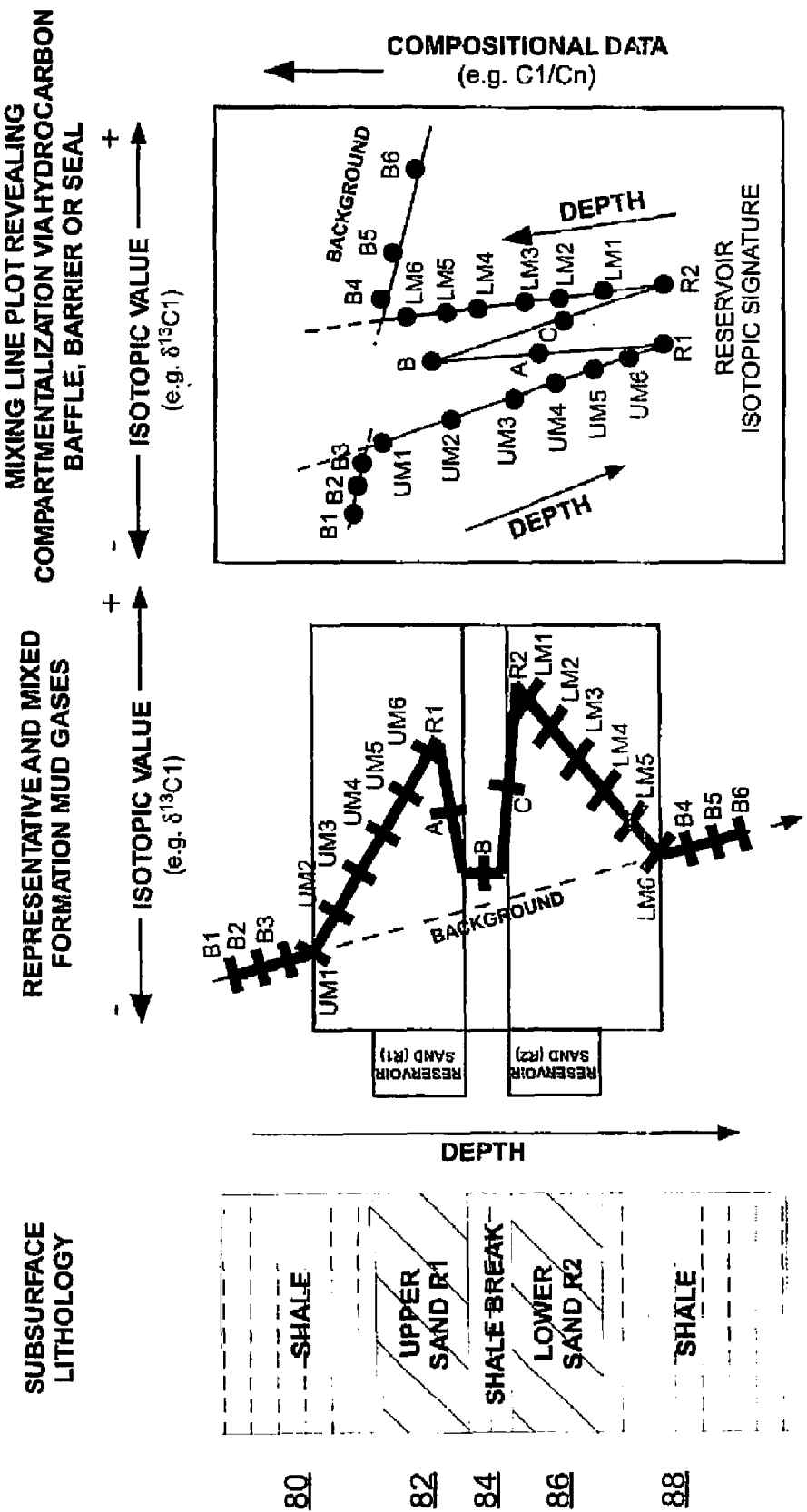

Formation Evaluation Log

| | REMARKS | LITHOLOGY |
|---|---|---|
| NC5(PPM) / IC5(PPM) / NC4(PPM) / IC4(PPM) / 10 100 1000 10000 | INCR MW 15.1PPG TO 15.3PPG @ 13533'MD, 13441'TVD | SLTST: lT GRY TO DK GRY, MOD FRM TO FRM, BLKY, GRTTY, DLL, SLI CALC |
| | INC 3.8, AZI 90_9 | BLKY, OCC TIKY TO SPM, ES TO DIL, SLI CALC |
| | WOB 6K, RPM 125 PP 4110, GPM 645 | SLTST: lT GRY TO DK GRY, MOD FRM TO FRM, BLKY, GRTTY, DLL |
| | SVY:13677'MD,13584'TVD INC 1.7, AZI 85.5 | SH: GRY TO DK GRY, FRM TO HD, BLKY, OCC BLKY TO SPLLN, OA TO |
| | SET 9 5/8" LINER @ 13765'MD 13673'TVD LOT-17.7PPG(E) | SLTST: lT GRY TO DK GRY, MOD FRM TO FRM, BLKY, DLL, V SDY, |
| | SVY:13773'MD,13681'TVD INC 0.4 CR@ 13801'MD INCR MW 15.3PPG | |
| | INCR MW 15.5PPG TO 15.7PPG @13883'MD, 13771'TVD | SD: CLR, UNCON, F TO M GR, TR CRS GR, SBANG TO MDD, MOD |
| | INCR MW 15.7PPG TO 15.8PPG @ 13875'MD, 13784'TVD CR @ | SLTST: lT GRY TO M GRY, FRM TO HD, BLKY, FLKY, GTTY, DIL, SIL CALC |
| | INCR MW 15.8PPG TO 15.9PPG @ 13939'MD, 13847'TVD STUCK PIPE | SD: CIR TO FROS TO lT GRY. F TO MD GR.SBRNDD TO SBANG. MOD |
| | INCR MW 15.9PPG TO 16.6PPG @ RRB #6 STC PDC 8.5', 7X15 | SLTST: GRY TO DK GRY, OCC lN, MOD FRM TO FRM, BLKY, GRTTY, |
| | SVY:14028'MD, 13936'TVD INC 0.6, AZI 341.8 | SH: GRY TO DK GRY, OCC TAN, FRM TO HD, BRIT, BLKY, GTTY, DLL, MOD |
| | MW 16.6,V 78,CL 42K | SH: GRY TO DK GRY, OCC BRN/GRY, FRM TO MOD HD, BRIT, BLKY, GTTY |
| | SVY:14123'MD,14031'TVD INC 0.5, AZI 325.3 | SDST: lT GRY TO GRY, CLR, MOD HD VT TO M GR, SBMDD TO SBANG, P SRTD, ALTY, TR DLL YET FLUOR, |
| | WOB 10K, RPM 150 PP 3920,GPM | |
| | SVY:14219'MD,14127'TVD INC 0.5, AZI 321.4 | SDST: lT GRY TO GRY, CIR, MOD HD, VF TO M GR, SBRNDD TO SBANG, P SRTD, AKY, 10% DLL YET FLUOR, |
| | MW 16.6, V 77, CL 43K | SDST: lT GRY TO GRY, CIR, FRI TO FRM, VF TO F GR, ABRNDD TO |
| | SVY:14305'MD, 14213'TVD INC 0.4, AZI 328.1 | SLTST: GRY TO DK GRY, FRM BRK, BLKY, DLL, ALL CAlC. ADY |
| | WOB 12K, RPM 150 | SDST: V lT GRY, CLR, TRT TO HD |

FIG. 12B

| DURING DRILLING | TYPICALLY AFTER DRILLING UNLESS USING LWD/ MWD TOOLS 404 | DURING DRILLING FROM MUD STREAM 406 |
|---|---|---|
| MUDLOG LOG | GEOPHYSICAL LOG | GAS ISOTOPE LOG |
| E.G. GAS LOGS, ROP, LITHOLOGY ETC.<br><br>TYPES<br>TOTAL GAS,<br>C2/C1,<br>C1,C2,C3 ETC<br>%SHALE/SAND ETC. | E.G. COMPLETION LOGS, ELECTRIC, SONIC, RADIOACTIVE, NMR ETC.<br><br>TYPES<br>RESISTIVITY, SONIC, GAMMARAY NMR NEUTRON ETC. | 13CN (CARBON ISOTOPES, N= 1 TO 5)<br>2H (HYDROGEN ISOTOPES)<br>GAS MATURITY<br>% THERMOGENIC<br>%MICROBIAL (BIOGENIC)<br>COMPARTMENTS (GOOD HYDROCARBON COMMUNICATION IN STRATA DERIVED FROM MIXING LINES)<br>SEALS, BARRIERS, BAFFLES (RESTRICTED HYDROCARBON COMMUNICATION IN STRATA DERIVED FROM MIXING LINES) |

FIG. 13

METHOD OF INTEGRATION AND DISPLAYING OF INFORMATION DERIVED FROM A MUD GAS ISOTOPE LOGGING INTERPRETATIVE PROCESS IN ASSOCIATION WITH GEOPHYSICAL AND OTHER LOGS FROM OIL AND GAS DRILLING OPERATIONS

RELATED APPLICATIONS

This application is a continuation-in-part application of co-pending U.S. patent application Ser. No. 10/952,136 entitled "MUD GAS ISOTOPE LOGGING INTERPRETATIVE PROCESS UTILIZING MIXING LINES IN OIL AND GAS DRILLING OPERATIONS" filed on Sep. 28, 2004 now U.S. Pat. No. 7,174,254 under the name of Leroy Ellis which is a continuation-in-part application of U.S. patent application Ser. No. 10/845,743, now U.S. Pat. No. 7,124,030 entitled "MUD GAS ISOTOPE LOGGING INTERPRETIVE METHOD IN OIL AND GAS DRILLING OPERATIONS" filed on May 14, 2004 under the name of Leroy Ellis and is hereby incorporated by reference.

BACKGROUND OF THE INVENTION

1. Field of the Invention

This invention relates to the presentation and display of mudlog and geophysical log data with hydrocarbon isotopic analysis data associated with oil and gas drilling operations. Specifically, the present invention relates to the display of an interpretive method derived from mud gas isotope logging data to assess hydrocarbon charge, source identification, maturity, reservoir compartmentalization and hydrocarbon communication concomitant with identification of lithological seals, baffles and barriers with conventional oil and gas exploration and production geophysical logs.

2. Description of the Related Art

Laboratory analysis of gas samples obtained during a drilling operation may be employed to determine geochemical information associated with strikes of oil or gas deposits. The laboratory analysis may include the acquisition of compositional and isotopic data of sampled subsurface gases. This data is applied to traditional geochemical plots and templates. The interpretation of this data is used to provide geochemical information on the oil and gas provenance, how thermally mature the hydrocarbons are, whether subsurface post-generation effects were encountered during migration of the gaseous hydrocarbons from the source rock to a reservoir, and any problems or effects the hydrocarbons in the reservoir subsequently experienced.

Existing well sampling techniques use physical gas samples for compositional and isotopic laboratory analyses, obtained via wellheads, separators, down-hole logging tools (e.g., modular dynamic tester/repeat formation tester, etc.), canned cuttings, and/or sampled gases entrained in the mud system during drilling.

As discussed in U.S. Pat. No. 7,124,030, there are several problems and issues not adequately addressed using standard mud gas chromatographic compositional analyses and interpretations. None of the existing techniques effectively detail or correlate geological information such as lithological hydrocarbon seals, baffles and barriers, good communication compartments, or gas diffusion and/or leakage into their interpretation. Compositional data can result in false positives and negatives where changes in operational conditions related to drilling variables such as increased rate of penetration or mud weight increases occur. U.S. Pat. No. 7,124,030 provides a far more advanced method which applies new interpretative techniques involving mud gas chromatographic compositional and isotopic analyses together with detailed drilling, geological and engineering information integration.

Within the improved interpretative techniques disclosed in U.S. Pat. No. 7,124,030 is the newly developed use of hydrocarbon mixing lines to determine or suggest good hydrocarbon communication compartments and zones. Mixing lines are identified on plots where hydrocarbon gas compositional and isotopic data are plotted. The mixing lines are defined by data points falling along a plotted trend line, suggesting a depth section in the well that is in good gas communication, and therefore representative of a compartment. Breaks in any of the mixing lines identify approximate depth locations at which lithological seals, baffles or other barriers to hydrocarbon communication may in fact be present. The depth range of each line may be considered to reflect or suggest an interval of good hydrocarbon communication. Furthermore, a number of seals, baffles and barriers are suggested defining these intervals, supporting the interpretation that these intervals may be likely to show localized hydrocarbon communication zones concomitant with potentially serious compartmentalization issues.

In the oil and gas industry, geophysical well logs have been invaluable in the search for oil and gas because they provide rapid, economical, and detailed information on whether a well is good or bad. A good well is commercially productive which produces enough oil or gas to pay back the cost of drilling and provides for a profit. A bad well is not commercially productive and can result in expensive losses. Oilfield logs are important tools to assist in making this determination. The mud log is used in combination with the electrical logs run on the well to make a decision about whether to complete the hole (i.e., try to produce oil or gas from it) or "plug" the well (i.e., filled with cement and abandoned). In addition, there are many different kinds of electric logs, and only those that provide the best data about the particular hole are likely to be selected and utilized.

Logs are displayed on a wide variety of individual charts/graphs on a long 'strip' of paper that are keyed to depths in the well, and may provide information on depth and thickness of strata/formations penetrated by a well, lithologic characteristics and types of formations encountered (such as shale, sandstone, limestone, dolomite), fluid content including presence of oil or gas, porosity, permeability, dip, reservoir pressure etc. The development of new logs, as well as new uses for old logs, is continuously changing.

Currently, there are several types of logs presently used in oilfield drilling operations. For example, there are mudgas logs which show drill time log (e.g., rate of penetration), mud weight, gas logs (e.g., showing total gas & gas chromatographic response of individual gas components together with cuttings logs (e.g., showing lithological description of cuttings such as sand/shale/siltstone/coal/halite etc. Additionally, there exists geophysical well logs which incorporate both electric and radioactive tools among others, and may include depth logs (e.g., MD and TVD, spontaneous potential, gamma ray, resistivity logs (e.g., conventional electrical survey, focused resistivity devices, induction logs, phaser induction logs, etc.), porosity logs (e.g., sonic or acoustic log, etc.), and neutron density logs.

While a well is being drilled, mudlogs are continually recorded. Recent development of 'measurement-while-drilling' (MWD) and 'logging-while-drilling' (LWD) logs may also be employed during drilling. After a well is drilled, "electric logging tools" may be lowered into the hole on a "wireline" that provides electrical power down to the "tools", and transmits the tool readings back up. All of these logs are currently utilized to determine rock types at given depths, and to indicate zones of porous rock.

It would be a distinct advantage to incorporate the interpretative techniques disclosed in U.S. Pat. No. 7,124,030 and U.S. patent application Ser. No. 10/952,136 with current mudlog and other geophysical logs. It is an object of the present invention to provide such a system and method.

SUMMARY OF THE INVENTION

In one aspect, the present invention is a method of displaying well log information in a drilling operation of a target area. Information from a gas isotope log is added to a formation evaluation log to analyze the targeted area in drilling operations. The method begins by profiling a plurality of mud gas samples through a well bore at a plurality of incremental depths of the well bore. The plurality of gas samples are analyzed to obtain a plurality of isotopic data points associated with hydrocarbon isotopic composition of the plurality of gas samples. The plurality of isotopic data points includes data associated with a composition of ethane and methane within each of the mud gas samples. The plurality of isotopic data points are plotted to determine geological information from the target area derived from the plotted plurality of isotopic data points. The plurality of isotopic data points are analyzed to geochemically interpret the geological information. The interpretation is then displayed in association with data from a mudlog and/or geophysical log.

BRIEF DESCRIPTION OF THE DRAWINGS

FIGS. 2A and 2B are an exemplary table illustrating tabulated data of a typical mud gas composition and gas isotope sampling data for a drilling well;

FIGS. 5A-5C illustrate the principles of the mixing processes in mud gas samples;

FIGS. 6A-6C illustrates the prediction of reservoir compartments and discontinuous reservoirs separated by seals, baffles or barriers via a thin shale lithology example;

FIGS. 12A and 12B are an exemplary existing formation evaluation log utilized to providing information on a well;

FIG. 13 is an informational block diagram of the log information utilized in current mudlog and geophysical logs with new information derived from a gas isotope log in the preferred embodiment of the present invention.

DESCRIPTION OF THE INVENTION

The present invention is a system and method of integrating and displaying information utilizing an interpretive method of mud gas isotope logging to determine hydrocarbon charge, source identification, maturity, reservoir hydrocarbon isotopic signature, good hydrocarbon communication, seals, baffles or other barriers to hydrocarbon communication in oil and gas drilling prospects.

Figure 1:
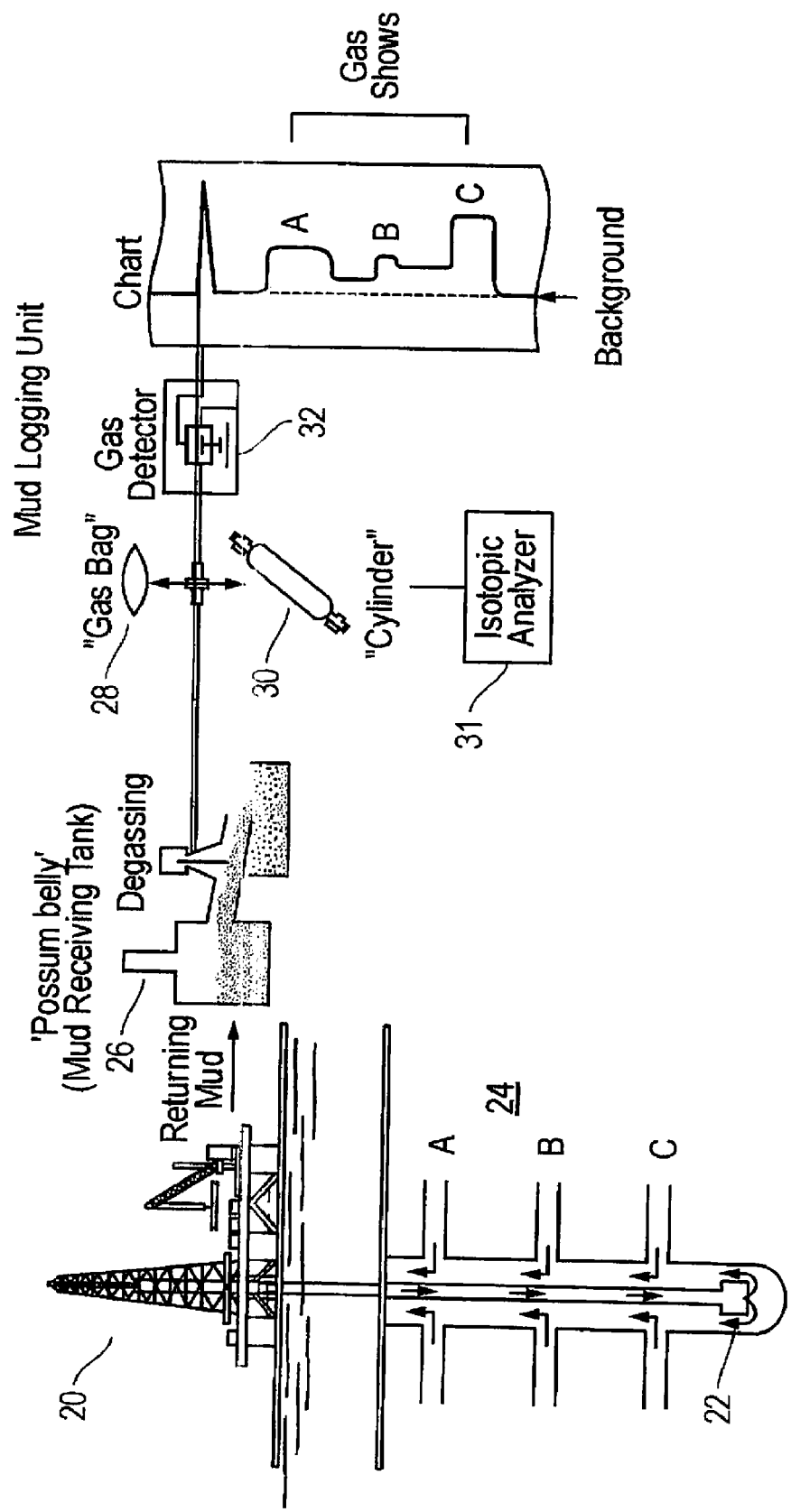
FIG. 1 is a block diagram illustrating principles of mud circulation during drilling operations and sampling of mud gases in the preferred embodiment of the present invention.

FIG. 1 is a block diagram illustrating principles of mud circulation during drilling operations and sampling of mud gases in the preferred embodiment of the present invention. A well 20 having a drill 22 drills down into the ground 24. Levels A, B, and C provide exemplary gas shows related to subsurface reservoirs. Mud is circulated around the drill 22 to provide lubrication for the drill and removing debris (cuttings) as it drills. The mud is circulated to the surface. The returning mud is collected on the surface within a mud receiving tank 26, also known as a possum belly. The gas is mechanically or otherwise degassed/exsolved form the mud and may be collected within a gas sampling device 28, a cylinder 30, or delivered to a mobile/onsite/in-situ isotopic analyzer 31. Typically, at a remote laboratory, mud logging unit, or an isotopic analyzer 31, a gas detector 32 (such as a gas chromatograph or mass spectrometer) is also utilized to measure compositional ratios of different hydrocarbon species.

In the preferred embodiment of the present invention, for a new drilling well, the samples are taken at regular depths (e.g., every 150-500 feet), throughout the entire well in order to establish a background trend, and more frequently in oil and gas show intervals. Once a background is established in a field, the spacing may be relaxed to a 500-foot or greater interval on later wells as more experience and knowledge is gained in the area. Additionally, gas samples collected in gas sampling devices typically see more restricted gas diffusion in the mud stream on the way to the surface as opposed to canned-cuttings that may smear, distribute or be collected over a wide composite depth interval in the mud system due to inherent density and fractal characteristic differences. Therefore, the sample depth recorded for the gas sampling devices is considered to more closely approximate the actual depth, whereas canned cuttings by nature may not accurately indicate the actual depth as rock density and fractal variables come into play in the mud system.

FIGS. 2A and 2B are an exemplary table illustrating tabulated data of a typical mud gas composition and gas isotope sampling data for a drilling well. As discussed above, samples are taken at regular intervals through the well. The gas compositional data and carbon isotopic data may be arranged in any fashion. As illustrated in FIG. 2, matching rows are characterized by depth of the samples.

Figure 3:
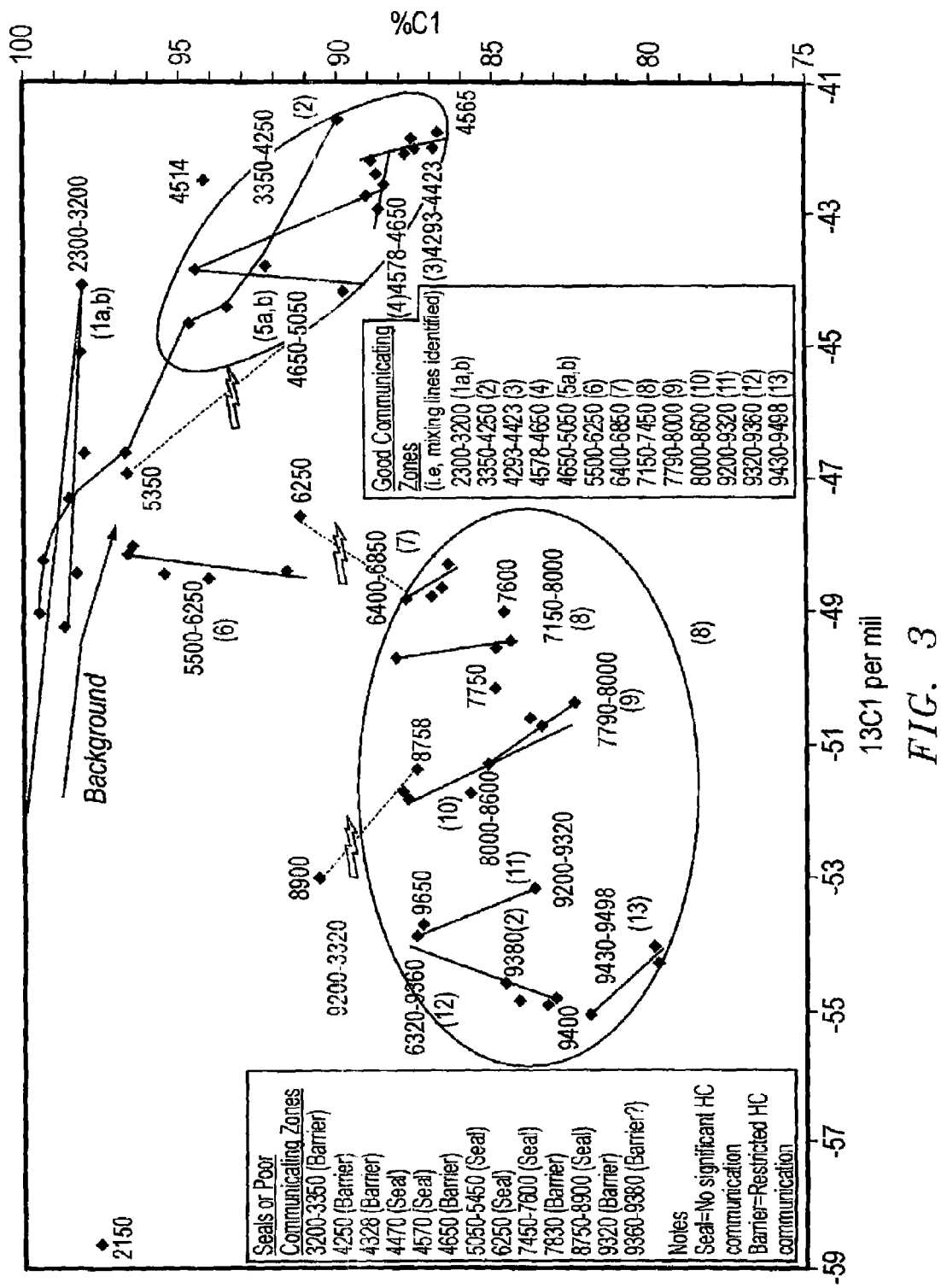
FIG. 3 is a chart illustrating a percentage C1 versus isotopic data chart in the preferred embodiment of the present invention.

FIG. 3 is a chart illustrating a percentage C1 versus corresponding and related isotopic data (e.g., $\delta^{13}C$, $^2H$) chart in the preferred embodiment of the present invention. Percentage C1 may be illustrated on the one axis (e.g., Y-axis) and isotopic data displayed on the other axis (e.g., x-axis). Straight lines (which usually are defined by at least three sequential depth data points) or other identified trends within the data are then identified and referred to as "mixing lines." These mixing lines equate to subsurface zones (compartments) in hydrocarbon gas communication. The points where the mixing lines start and end typically reveal "breaks" which may equate to lithological hydrocarbon communication seals, baffles or barriers. Baffles and barriers typically occur where a simple break in a mixing line occurs. Seals typically occur where the break is significant and the next depth data point deviates substantially. Either the next mixing line reverses direction or the next data point is far removed from the previous depth data point or mixing line. If the next (adjacent) mixing line reverses direction from one mixing line to another mixing line, this may represent one compartment where the point of reversal between the mixing lines may be representative of the actual reservoir hydrocarbon isotopic signature. If the next (adjacent) mixing line is substantially deviated, then a lithological seal, baffle or barrier may be indicated. FIG. 3 may include depth range labeling for any mixing line. Additionally, straight line-of-best-fit may also be drawn for data approximating a mixing line. Data groups that are tightly clustered are similarly interpreted to indicate good communication zones, analogous to mixing lines.

Figure 4:
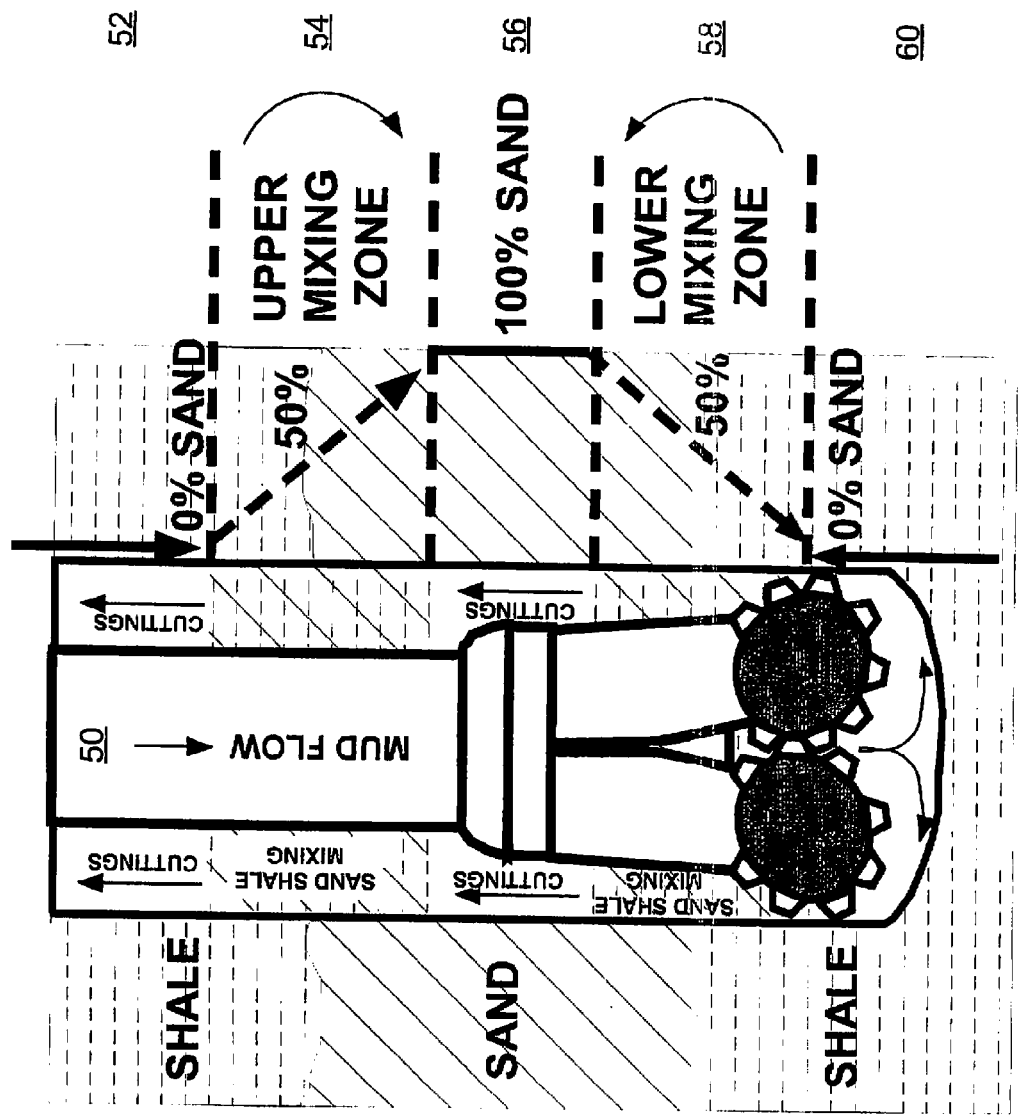
FIG. 4 is an example lithology illustrating the principles of lithology mixing of drilling cuttings in mud-stream at sand/shale boundaries.

FIGS. 4-11, discussed below, provide an explanation and illustrate examples of the principles involves in interpreting the data. FIG. 4 is a lithology illustrating the mixing of cuttings in a mud stream at sand/shale boundaries. Mud flows from a drill bore 50 (associated with drill 22) and moves upward as illustrated. As shown in FIG. 4, an upper shale area 52 overlays an upper mixing zone 54, a sand region 56, a lower mixing zone 58, and a lower shale area 60. The shale cuttings may mix with the sand region from above due to the higher density of the shale cuttings. The shale cuttings from the lower shale area may also invade the sand region due to higher frictional and fractal characteristics.

FIGS. 5A-5C illustrate the principles of related gas mixing processes entrained in drilling muds. FIG. 5A illustrates the lithology by showing the upper shale area 52, the sand region 56, and the lower shale area 60. The shales from the upper shale area 52 tend to cave. Specifically, shales may sink into the sand region due to lower buoyancy and higher density (more solids per volume) characteristics. Shale in the lower shale area 60 may upwell into the sand region due to higher frictional and/or fractal characteristics (more drag upwards; more particles/volume mud). FIG. 5B illustrates a chart showing depth versus $\delta^{13}C_1$. FIG. 5C is a gas mixing plot showing C1/Cn versus $\delta^{13}C_1$ or other isotopic data. The intersection of the top and bottom of the mixing line determines reservoir composition of one continuous reservoir where the point of reversal between the mixing lines may be representative of the actual reservoir hydrocarbon isotopic signature. The mixing of lithologies results in the mixing of gases. Mixing plots allow differentiation between hanging and footwall mixing.

FIGS. 6A-6C illustrates the prediction of reservoir compartments and discontinuous reservoirs separated by a thin shale, other lithology or geological phenomena. FIG. 6A illustrates the lithology showing an upper shale region 80, a sand region 82, a shale break 84, a sand region 86, and a lower shale region 88. Within the sand region 82 is a reservoir R1. Within the sand region 86 is a second reservoir R2. In a similar manner as FIG. 5B, FIG. 6B illustrates the processes of gas mixing and expected isotopic mixing trends in a reservoir separated by a thin shale. FIG. 6C illustrates a gas mixing plot showing C1/Cn versus $\delta^{13}C_1$.

Figure 7:
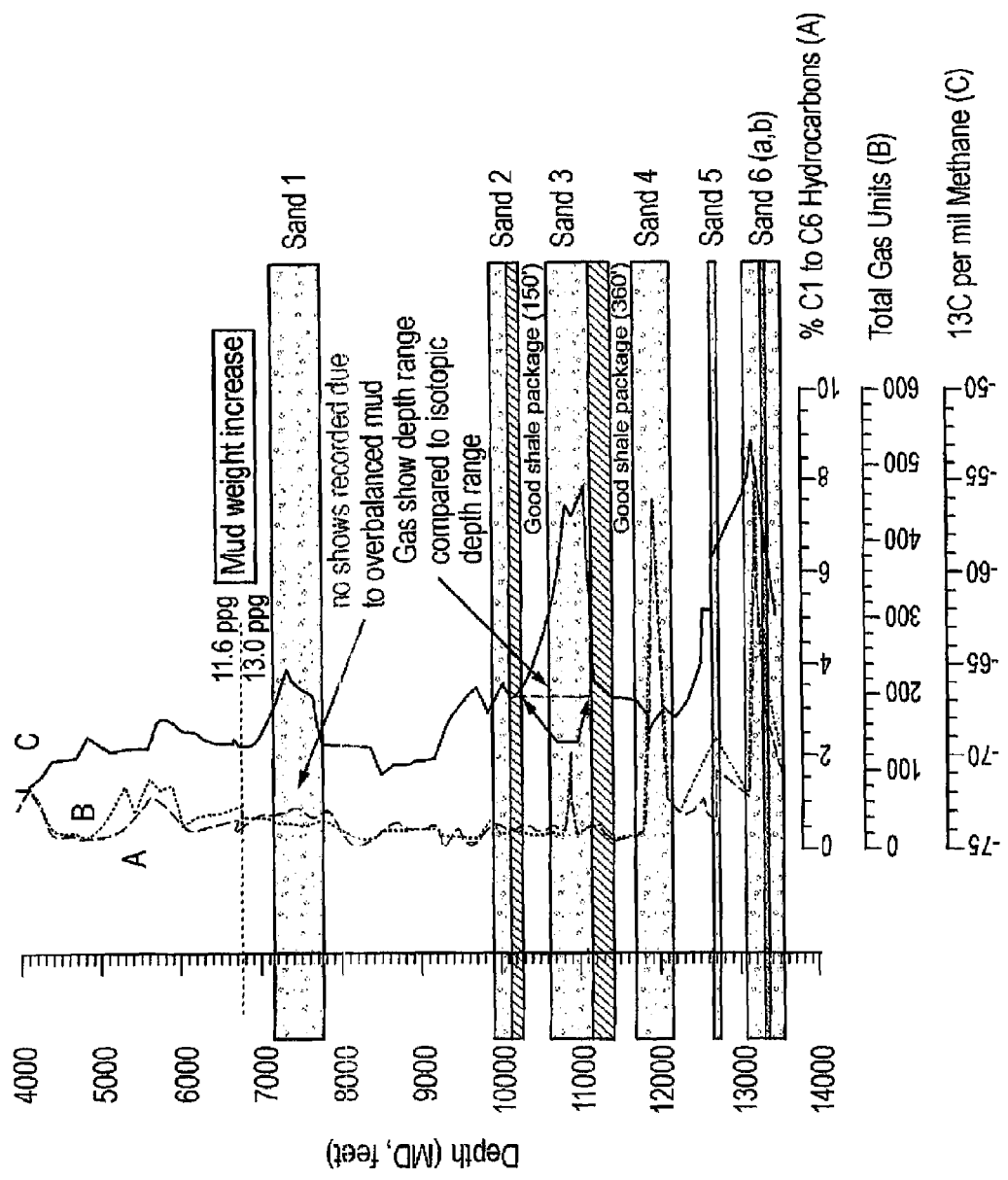
FIG. 7 illustrates an example drilling well log formed by a percentage summed C1 to C6 hydrocarbons, gas units, and 13C methane isotopic data at various depths.
Figure 8:
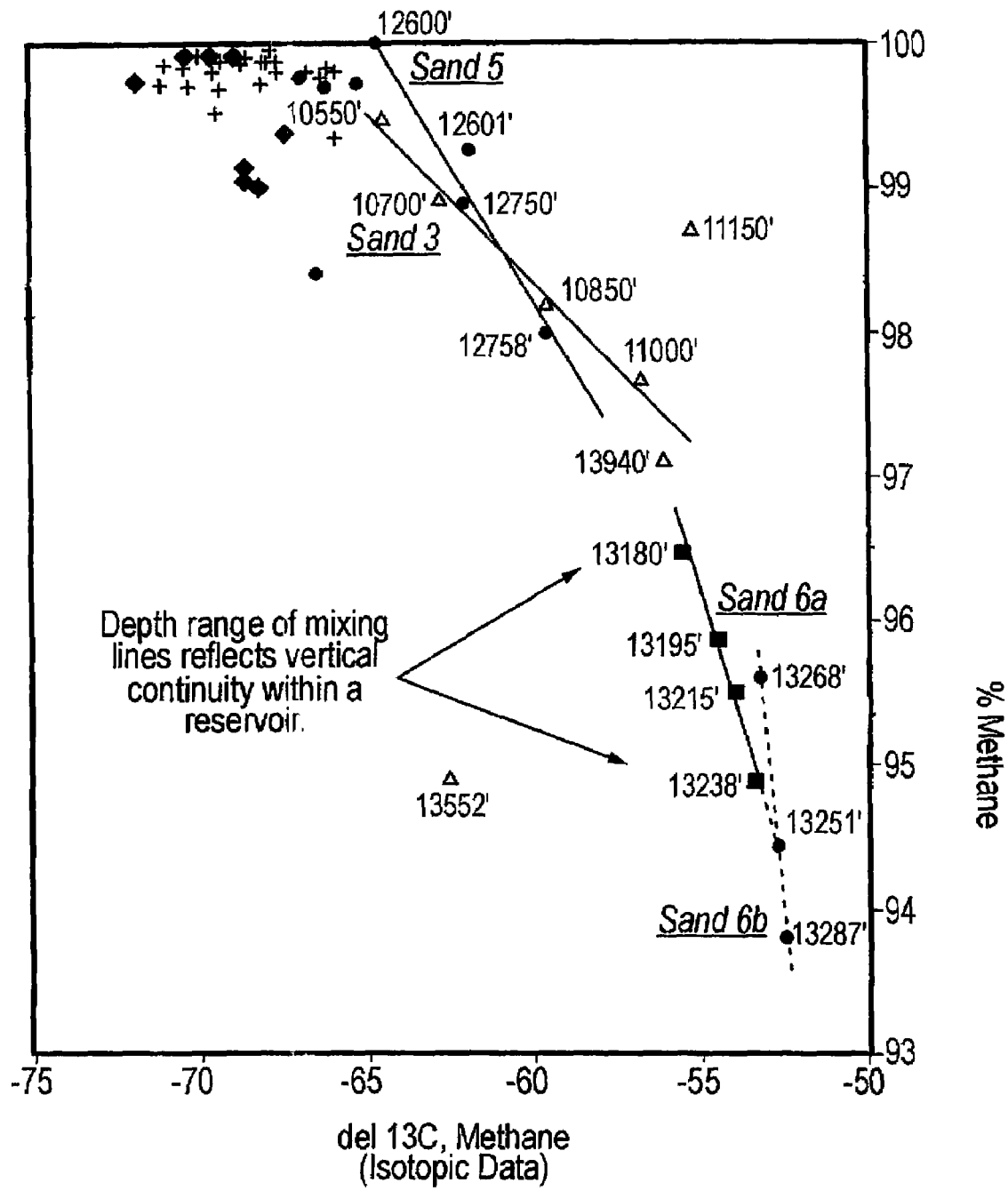
FIG. 8 illustrates a first exemplary gas mixing plot showing C1/Cn versus $\delta^{13}C_1$.
Figure 9:
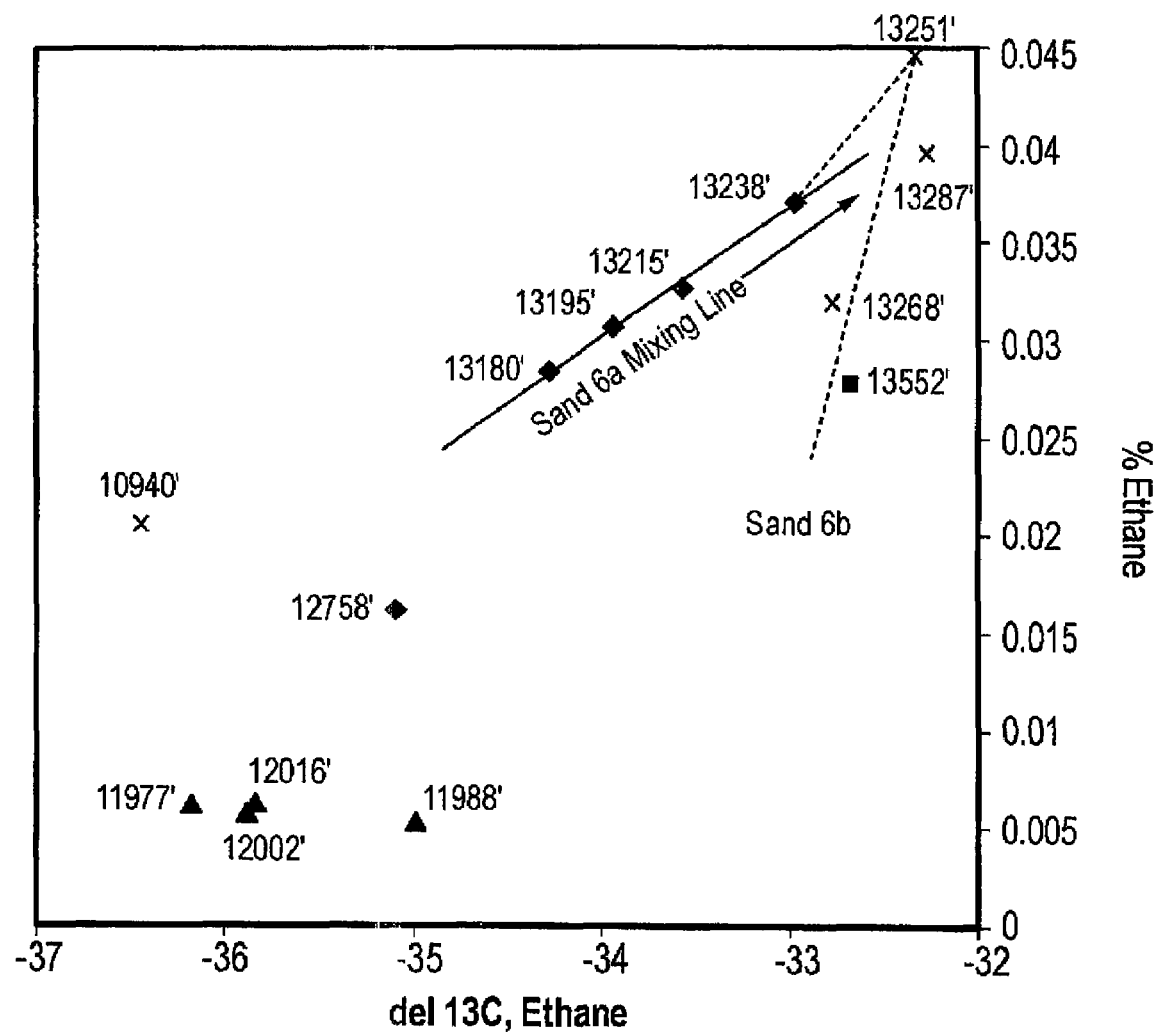
FIG. 9 illustrates a second exemplary gas mixing plot showing C2/Cn versus $\delta^{13}C_2$.

FIG. 7 illustrates an example drilling well log formed by percentage C1 to C6 hydrocarbons, gas units and isotopic data at various depths. FIG. 7 provides a real-world example of missed-pay, charge recognition, biodegradation and seal identification. An absence of gas shows also recognizes missed-pay potential due to operational drilling variables such as overbalanced mud weight. An absence of an isotopic show may be indicative of a non-economical background gas-charged sand or biodegraded gas/oil mixture. An isotopic peak profile may also recognize gas cap seal integrity in reservoirs. Gas shows correspond to isotopic shows in typical charged sands. Sand 6 illustrates thin shale in sand, which results in compartmentalization. FIGS. 8 and 9 show associated mixing lines.

FIG. 8 illustrates a gas mixing plot showing C1/Cn versus $\delta^{13}C_1$. Sands 3 and 5 (see FIG. 7) form closely approximating mixing lines, which indicate a possible relationship between these reservoirs. Sand 6a forms a good mixing line down to approximately 13251 feet, which while still within the reservoir suggests that this reservoir is compartmentalized. Separation of the mixing lines 6a and 6b illustrates identification of a seal, baffle or barrier between 13238 feet and 13251 feet. The depth range of mixing lines reflects vertical continuity within each reservoir.

FIG. 9 illustrates a gas mixing plot showing C2/Cn versus $\delta^{13}C_2$. This plot, similar to FIG. 8 employs ethane (C2) compositional and associated isotopic data to provide an early assessment of reservoir continuity and compartmentalization. Sand 6a represents a mixing line, whereas sand 6b is, at best, a different mixing line. Sand 6a mixing line terminates at a point between 13238 feet and 13251 feet (similar to FIG. 8) suggesting that a seal, baffle or barrier to communication may be present. Sand 6a and 6b appear to be separate compartments with zero or limited gas communication. The identification of a seal, baffle or barrier between 13238 feet and 13251 feet using ethane data further supports and validates similar interpretations arrived at in FIG. 8 using methane compositional and isotopic data.

Figure 10:
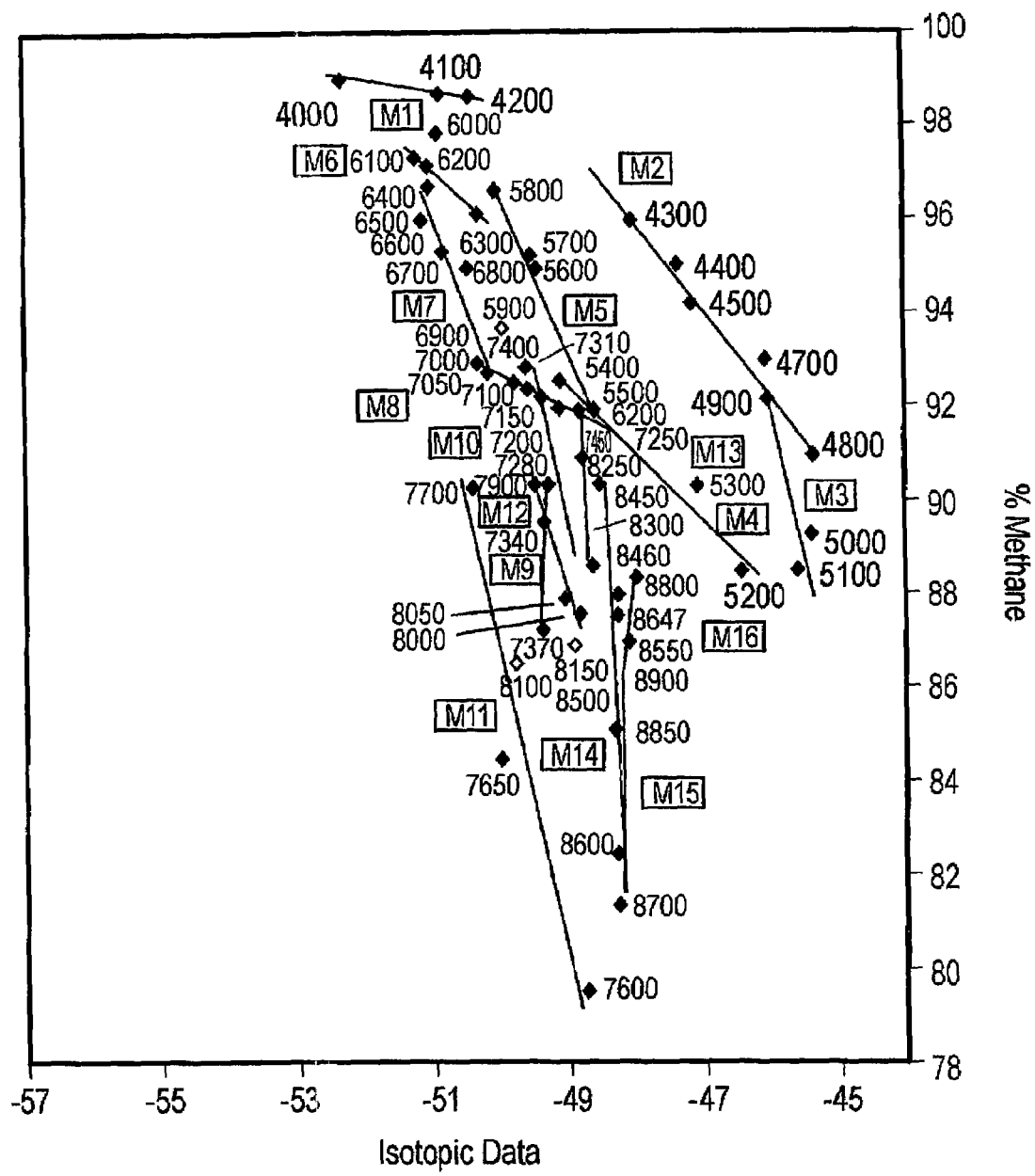
FIG. 10 illustrates a third exemplary gas mixing plot showing C1/Cn versus $\delta^{13}C_1$.

FIG. 10 illustrates another real-world example of a gas mixing plot showing C1/Cn versus $\delta^{13}C_1$ and shows an early assessment of reservoir continuity, compartmentalization and hydrocarbon communication. Mixing lines are easily recognized with the resulting depth range of lines reflecting separate compartments and continuity. The recognition of breaks (e.g. reference number 100) between related depth intervals (i.e., formation of separate mixing lines) suggests that a baffle or other lithological barrier to communication may exist. Mixing processes of sands and shales (e.g. reference number 200) in the circulating mud stream can also be observed.

Figure 11:
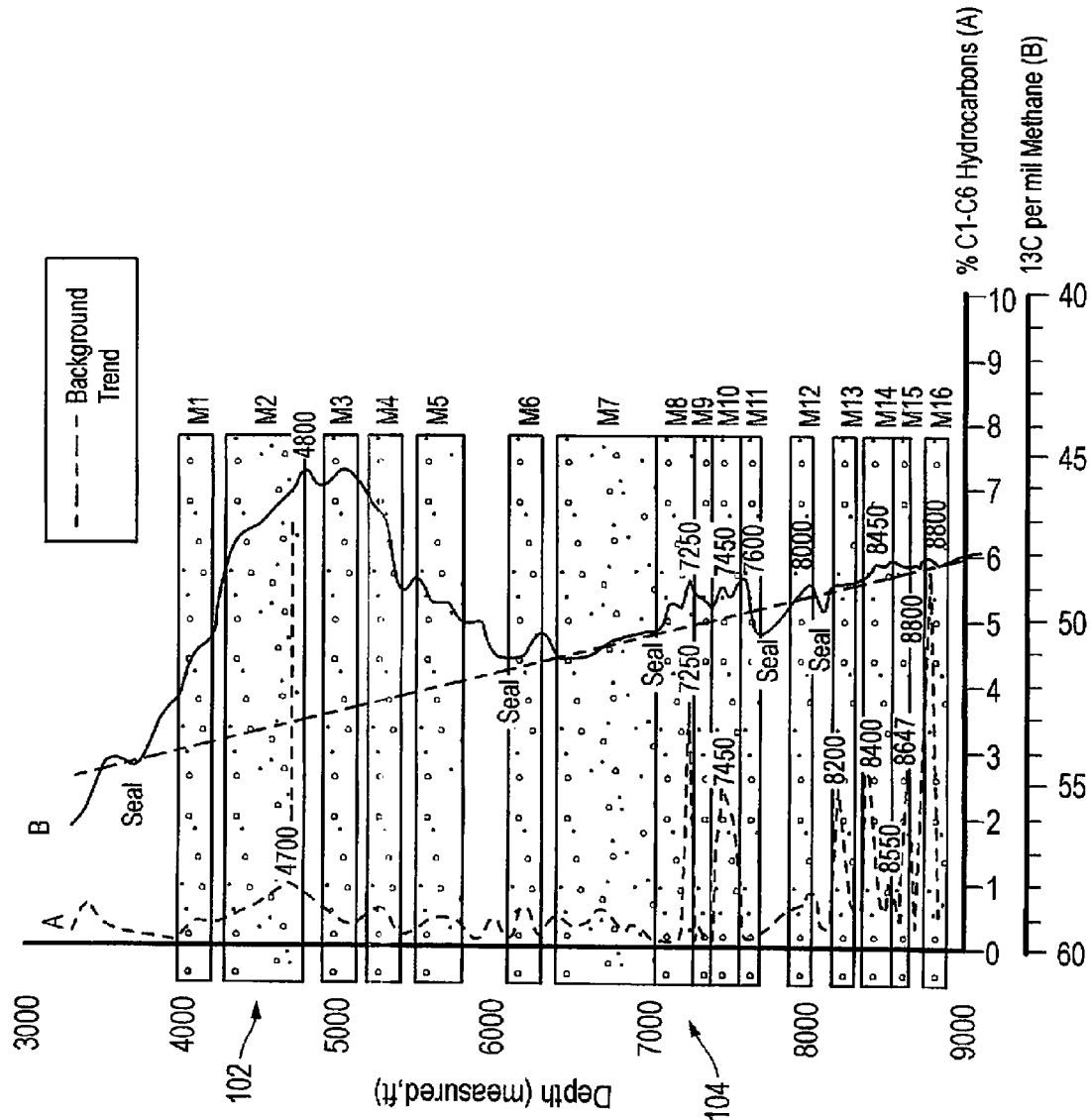
FIG. 11 illustrates an example well log formed by percentage C1-C6, gas units, and 13C methane.

FIG. 11 illustrates an example log percentage C1-C6 and 13C methane isotopic data. There are sixteen distinct gas communication compartments interpreted and identified. Reference number 102 shows the mixing line depth ranges superimposed on the gas compositional and isotopic log depths. Reference number 104 shows where isotopic shows and the gas shows agree.

The interpretive methodology may be used for reservoir seal identification. Seal integrity measured as a function of its ability to restrict reservoir gas diffusion or other hydrocarbon leakage may be observed through mud gas isotope logging. Data from wells may indicate diffusion or leakage of reservoir gases into formations both above and below identified reservoirs. This data present and support potential identification of low- and high gas reservoir saturations. Low gas saturations are commonly ascribed to leaky seals. If there is a leaky seal, the gas in the overlying seal interval may develop an isotopic signal similar to that of the underlying reservoir gas, and in contrast to the background shale methane and ethane isotopic ratios. In contrast, an intact seal may have some mixing a short interval above the reservoir, but overall, the overlying lithology should have a lighter, more constant methane and ethane isotopic signal. Therefore, an intact seal as discussed above may indicate high gas saturation, combined with a distinctly different gas isotopic signature in the reservoir. Seals that are intact, and seals that leak, may be identifiable from a change in background isotopic signatures (See FIGS. 4 and 5). This provides calibration between physical property measurements of the shales or other caprocks and their ability to seal. Seals, however, may only be identified/recognized using this technique over a depth interval in which appropriate detailed mud gas isotope logging data have been acquired. This hydrocarbon diffusion or leakage process is likely to occur over geologic time and terminates upon contact with an impermeable barrier such as a continuous/homogeneous dense and compacted lithology (e.g. shale, marl, chalk, or other geological phenomena with associated pore pressure changes) of low porosity/permeability. Seals such as these may be generally referred to as 'trapping' seals, or more specifically as, 'regional' or 'localized' seals depending on their stratigraphic extent. These seals represent barriers to the potential migration of hydrocarbons. Identification of seals is important in establishing potential migration pathways and reservoir compartmentalization. Reservoir sands within identified particular regional seals are likely to contain gases of the same type and maturity.

Reservoir seals are not as well understood as either source or reservoir rocks, and evaluating and predicting reservoir seals remain problematic. Within this context, mud gas isotope logging is a promising technique for both complementing existing seal analysis methodology and empirically verifying the presence of any seal, regardless of origin.

Mud gas isotope logging is a noninvasive technique used to evaluate exploration and field production. Isotopic measurements made on mud gas samples from either side of a potentially sealing interval can be used to determine the effectiveness of a seal as well as establish likely migration pathways and reservoir compartmentalization. For example, in a thermogenic gas reservoir associated with a leaky seal, gas in the overlying seal may develop an isotopic signature similar to that of the underlying reservoir gas. This leaky seal isotopic signature will be isotopically heavier and contrast with methane and ethane isotopic ratios in background shales. In contrast, an effective seal in this same thermogenic setting will have an isotopically lighter and more constant methane and ethane signal. By measuring changes in background isotopic signal of intact seals vs. seals that leak, calibration between physical property measurements of the seals and their ability to seal can be determined.

Figure 12A:
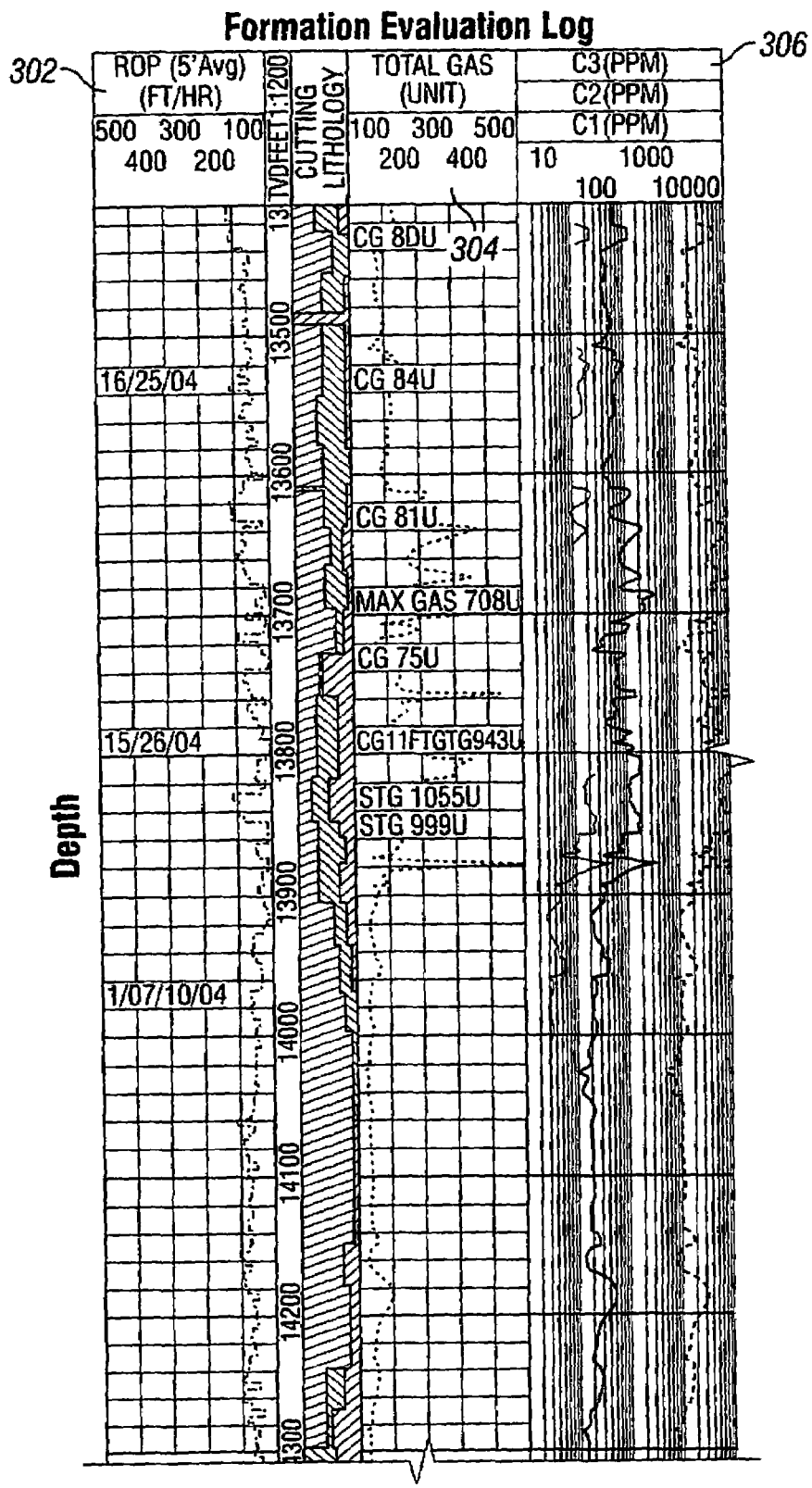

FIGS. 12A and 12B are an exemplary existing log 300 utilized to providing information on a well. As discussed above, logs are displayed on a wide variety of individual charts/graphs on a long 'strip' of paper that are keyed to depths in the well, and may provide information on depth and thickness of strata/formations penetrated by a well, lithologic characteristics and types of formations encountered (such as shale, sandstone, limestone, dolomite), fluid content including presence of oil or gas, porosity, permeability, dip, reservoir, pressure, etc. The development of new logs, as well as new uses for old logs, is continuously changing. For example, FIG. 12 provides a portion of the strip of the log 300. The log 300 includes a plurality of columns for displaying information, such as column 302 (ROP data), column 304 (total gas), columns 306 and 308 (carbon data), column 310 (remarks), and column 312 (lithology). The information is listed for a depth 312 which is depicted upon a vertical axis. The above information may be listed in other forms, but in the most common form, data is listed abeam each other for each particular depth to provide ease in analyzing well log information.

The present invention incorporates the novel interpretive methodologies disclosed in U.S. Pat. No. 7,124,030 and U.S. patent application Ser. No. 10/952,136 with current geophysical logs, such as illustrated in FIG. 12. FIG. 13 is an informational block diagram 400 of the log information utilized in current geophysical logs with the information gathered in the interpretive methodologies disclosed in U.S. Pat. No. 7,124,030 and U.S. patent application Ser. No. 10/952, 136. One or more columns 402 of the log may include mudgas data. The column 402 may include gas logs, ROP, lithology, etc. and include information on total gas, C2/C1, C1, C2, C3, % shale/sand, etc. Adjacent the mudlog column(s) 402 is information on the geophysical log 404 (e.g., completion logs, electric, sonic, radioactive, NMR, etc.). Different types of logs may include information on resistivity, sonic, gamma ray, NMR, neutron and other data pertinent to a well. The present invention now provides column 406, which may include gas isotope log information such as 13Cn (carbon isotopes, n=1 to 5), 2H (hydrogen isotopes), gas maturity, % thermogenic, % microbial (biogenic), compartments (good hydrocarbon communication in strata derived from mixing lines), and seal, barriers and baffles (restricted hydrocarbon communication in strata derived from mixing lines).

Figure 14:
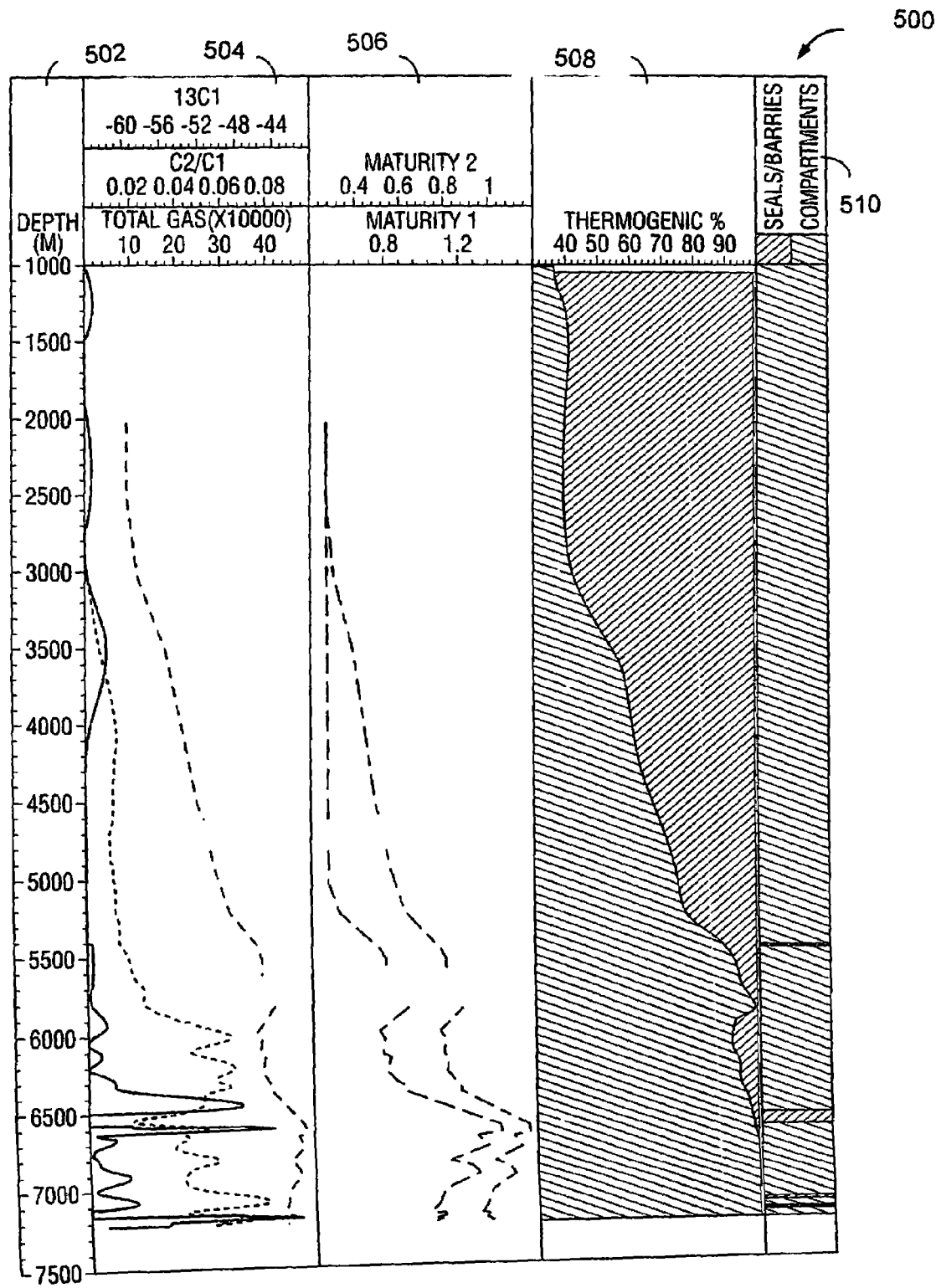
FIG. 14 is an exemplary log 500 of the present invention.

FIG. 14 is an exemplary log 500 of the present invention. The log 500 includes a depth column 502, a gas isotope log column 504, a maturity column 506, a thermogenic data column 508 and a column 510 providing information on seals/barriers (compartments, etc.).

The present invention provides all this information adjacent to each other at specific depths along side current log information to provide assistance in analyzing a well. The gas isotope logs may be utilized to verify other logs and enhance interpretation of information gathered from a well log. In addition, new interpretations, such as compartments and seals may be utilized to help define reservoirs containing hydrocarbons and seals that define migration pathways in the subsurface. Additionally, new interpretations may be added, such as percent thermgenic and percent microbial data to assist in characterizing hydrocarbons in the subsurface.

The present invention may take an existing formation evaluation log having a plurality of columns depicting various types of information versus a depth and add one or more columns providing gas isotope log information as discussed above. The additional column matches data at various depths. As depth increases, the information is provided at the relevant depth which may include mudgas information, geophysical information and the newly added gas isotope log information.

It should be understood, that the log display of FIG. 13 is exemplary of the present invention. Columns and order may vary and still remain within the scope of the present invention. In addition, although depth is depicted on the Y-axis of the log and column information on the X-axis, in alternate embodiments of the present invention, the present invention may include depth depicted on the X-axis and column data on the Y-axis.

The present invention provides many advantages to existing logs used in the oil and gas industry. The present invention supplies newly developed gas isotopic logs providing added and enhanced information for verifying various interpretations of current well logs while providing additional information for effectively and accurately predicting or suggesting good hydrocarbon communication (compartments), barriers, and seals.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

Thus, the present invention has been described herein with reference to a particular embodiment for a particular application. Those having ordinary skill in the art and access to the present teachings will recognize additional modifications, applications and embodiments within the scope thereof.

It is therefore intended by the appended claims to cover any and all such applications, modifications and embodiments within the scope of the present invention.

What is claimed is:

1. A method of displaying well log information in a drilling operation of a target area, said method comprising the steps of:
    obtaining a plurality of mud gas samples from a target area;
    analyzing the plurality of mud gas samples to obtain hydrocarbon compositional and isotopic data from the samples;
    plotting the hydrocarbon compositional and isotopic data upon a chart or well log;
    determining a trend of a plurality of points upon the chart;
    deriving from the chart or log an interpretation of the log indicative of hydrocarbon communication; and
    displaying the interpretation on a formation evaluation log.

2. The method of displaying well log information of claim 1 wherein mud gas and geophysical information is listed in column form adjacent the derived interpretation of the log at various depths of the targeted area.

3. The method of displaying well log information of claim 2 wherein the derived interpretation of the log includes gas isotopic data.

4. The method of displaying well log information of claim 2 wherein the gas isotope data is utilized to verify information from the mudgas and geophysical information.

5. A method of displaying well log information in a drilling operation of a target area, said method comprising the steps of:
    profiling a plurality of mud gas samples through a well bore at a plurality of incremental depths of the well bore;
    analyzing the plurality of gas samples to obtain a plurality of isotopic data points associated with hydrocarbon isotopic composition of the plurality of gas samples, the plurality of isotopic data points includes data associated with a composition of ethane and methane within each of the mud gas samples;
    plotting the plurality of isotopic data points;
    determining geological information from the target area derived from the plotted plurality of isotopic data points;
    analyzing the plurality of isotopic data points to geochemically interpret the geological information; and
    displaying the interpretation on a formation evaluation log.

6. The method of displaying well log information of claim 5 wherein mud gas and geophysical information is listed in column form adjacent the derived interpretation of the log at various depths of the targeted area.

7. The method of displaying well log information of claim 6 wherein the derived interpretation of the log includes gas isotopic data.

8. The method of displaying well log information of claim 6 wherein the gas isotope data is utilized to verify information from the mudgas and geophysical information.

\* \* \* \* \*